United States Patent
Uemura (10) Patent No.: US 10,471,245 B2
(45) Date of Patent: Nov. 12, 2019

(54) MANUFACTURING METHOD OF NEEDLE-SHAPED BODY, AND NEEDLE-SHAPED BODY

(71) Applicant: TOPPAN PRINTING CO., LTD., Taito-ku (JP)

(72) Inventor: Daizo Uemura, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 308 days.

(21) Appl. No.: 15/355,264

(22) Filed: Nov. 18, 2016

(65) Prior Publication Data
US 2017/0065804 A1 Mar. 9, 2017

Related U.S. Application Data

(63) Continuation of application No. PCT/JP2015/002324, filed on May 7, 2015.

(30) Foreign Application Priority Data

May 20, 2014 (JP) .................... 2014-104429

(51) Int. Cl.
*A61M 37/00* (2006.01)
*B29C 59/02* (2006.01)
(Continued)

(52) U.S. Cl.
CPC ........ *A61M 37/0015* (2013.01); *A61M 37/00* (2013.01); *B29C 37/0053* (2013.01);
(Continued)

(58) Field of Classification Search
CPC ...... A61M 37/0015; A61M 2037/0053; A61M 2037/0023; A61M 2037/0061; B29C 37/0053
See application file for complete search history.

(56) References Cited

U.S. PATENT DOCUMENTS 6,183,434 B1 2/2001 Eppstein
6,835,184 B1 12/2004 Sage et al.
(Continued)

FOREIGN PATENT DOCUMENTS

JP 2001-157715 A 6/2001
JP 2001-309977 A 11/2001
(Continued)

OTHER PUBLICATIONS

International Search Report dated Jun. 2, 2015 in PCT/JP2015/002324, filed May 7, 2015.

*Primary Examiner* — Lauren P Farrar
(74) *Attorney, Agent, or Firm* — Oblon, McClelland, Maier & Neustadt, L.L.P.

(57) ABSTRACT

A method of manufacturing a needle-shaped body includes forming a needle-shaped body precursor such that the needle-shaped body precursor has a base portion and a needle-shaped portion on the base portion, and that the needle-shaped portion has a portion which contacts the base portion and has a form of a polygon, producing a needle-shaped body original plate by forming a curved surface portion in at least a portion of an apex portion of the polygon in a junction portion at a boundary between the base portion and the needle-shaped portion, producing a resin plate by transfer molding with the needle-shaped body original plate such that the resin plate has a concave pattern corresponding to the needle-shaped portion and the curved surface portion, and producing a needle-shaped body by transfer molding with the resin plate such that the needle-shaped body has a transferred needle-shaped portion and a transferred curved surface portion.

20 Claims, 9 Drawing Sheets

(51) Int. Cl.
  *B29C 37/00*   (2006.01)
  *B29K 67/00*   (2006.01)
  *B29L 31/00*   (2006.01)

(52) U.S. Cl.
  CPC ... *B29C 59/022* (2013.01); *A61M 2037/0023* (2013.01); *A61M 2037/0053* (2013.01); *B29K 2067/043* (2013.01); *B29L 2031/756* (2013.01); *B29L 2031/7544* (2013.01)

(56) References Cited

U.S. PATENT DOCUMENTS

| | | |
|---|---|---|
| 7,347,835 B2 | 3/2008 | Maenosono et al. |
| 2003/0199811 A1 | 10/2003 | Sage, Jr. et al. |
| 2006/0127465 A1 | 6/2006 | Maenosono et al. |
| 2006/0264893 A1 | 11/2006 | Sage, Jr. et al. |
| 2008/0157421 A1 | 7/2008 | Mukai et al. |
| 2009/0036826 A1 | 2/2009 | Sage, Jr. et al. |
| 2012/0078189 A1* | 3/2012 | Ogawa .............. A61M 37/0015 604/173 |

FOREIGN PATENT DOCUMENTS

| | | |
|---|---|---|
| JP | 2005-021677 A | 1/2005 |
| JP | 2008-11959 A | 1/2008 |
| JP | 2012-143978 A | 8/2012 |
| JP | 2012-196426 A | 10/2012 |
| WO | WO 2006/077742 A1 | 7/2006 |
| WO | WO 2013/171907 A1 | 11/2013 |

* cited by examiner

MANUFACTURING METHOD OF NEEDLE-SHAPED BODY, AND NEEDLE-SHAPED BODY

CROSS-REFERENCE TO RELATED APPLICATIONS

The present application is a continuation of International Application No. PCT/JP2015/002324, filed May 7, 2015, which is based upon and claims the benefits of priority to Japanese Application No. 2014-104429, filed May 20, 2014. The entire contents of these applications are incorporated herein by reference.

BACKGROUND OF THE INVENTION

Field of the Invention

The present invention relates to a manufacturing method of a needle-shaped body, and a needle-shaped body.

Discussion of the Background

In a method for allowing a body to effectively absorb a medicine which is difficult to administer, for example, a micrometer-order fine needle-shaped body (i.e., microneedle) is used to perforate the skin and directly administer the medicine into the skin. For example, PTLs 1 to 4 describe techniques related to a needle-shaped body used for the above-mentioned method.
PTL 1: U.S. Pat. No. 6,183,434 B1
PTL 2: JP-A-2005-021677
PTL 3: JP-A-2001-309977
PTL 4: JP-A-2012-143978

SUMMARY OF THE INVENTION

According to one aspect of the present invention, a method of manufacturing a needle-shaped body includes forming a needle-shaped body precursor such that the needle-shaped body precursor has a base portion and a needle-shaped portion on the base portion, and that the needle-shaped portion has a portion which contacts the base portion and has a form of a polygon, producing a needle-shaped body original plate by forming a curved surface portion in at least a portion of an apex portion of the polygon in a junction portion at a boundary between the base portion and the needle-shaped portion in the needle-shaped body precursor, producing a resin plate by transfer molding with the needle-shaped body original plate such that the resin plate has a concave pattern corresponding to the needle-shaped portion and the curved surface portion in the needle-shaped body original plate, and producing a needle-shaped body by transfer molding with the resin plate such that the needle-shaped body has a transferred needle-shaped portion having a shape of the needle-shaped portion transferred and a transferred curved surface portion having a shape of the curved surface portion transferred.

According to another aspect of the present invention, a needle-shaped body includes a base portion, a needle-shaped portion formed on the base portion, and a curved surface portion formed in at least a portion of a junction portion at a boundary between the base portion and the needle-shaped portion. The needle-shaped portion has a portion which contacts the base portion and has a form of a polygon, and the curved surface portion is formed in an apex portion of the polygon in the junction portion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

Hereinafter, with reference to the drawings, a needle-shaped body and a manufacturing method of a needle-shaped body will be described. In the following detailed description, various specific portions are described so as to provide complete understanding of the embodiment of the present invention. However, it is apparent that one or more embodiments can be embodied without such specific details. Further, known structures and apparatus are schematically illustrated to simplify the drawings. Further, in the respective drawings, the same reference signs are assigned to elements having the same or similar functions to omit duplicate description.

Manufacturing Method of Needle-Shaped Body

A manufacturing method of a needle-shaped body according to the present embodiment is configured of a process of forming a precursor of a needle-shaped body, a process of producing a needle-shaped body original plate, a process of producing a resin plate, and a process of producing a needle-shaped body.

The precursor of the needle-shaped body is provided with a base portion, and a needle-shaped portion on the base portion in which a portion contacting the base portion is formed into a polygon. The needle-shaped body original plate is produced by forming a curved surface portion having a curved surface formed into a convex shape, at at least a part of the periphery of a joint portion where the base portion of the precursor of the needle-shaped body is jointed to the needle-shaped portion. The resin plate is produced by transferring the needle-shaped body original plate so that the resin plate has a concave portion with a shape corresponding to the needle-shaped body original plate.

FIGS. 1(a)-1(f) and 1(g)-1(l) are manufacturing process diagrams illustrating a manufacturing method of the needle-shaped body according to the present embodiment. Hereinafter, manufacturing processes illustrated in FIGS. 1(a)-1(f) and 1(g)-1(l) will be described in the order of the manufacturing process steps.

Step of Forming a Needle-Shaped Body Precursor

Figure 1A:
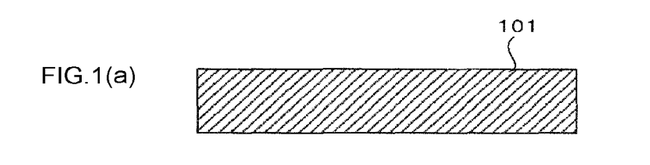
FIGS. 1(a)-1(f) are process charts showing a manufacturing method of a needle-shaped body according to an embodiment of the present invention.
Figure 1B:
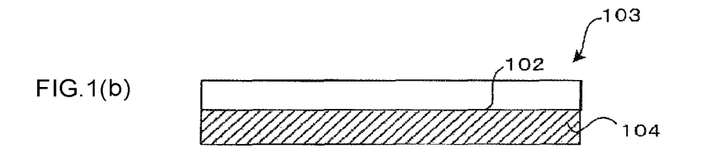
Figure 1C:
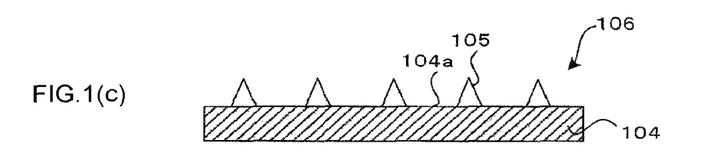

FIGS. 1(a) to 1(c) are cross-sectional views showing a step of producing a needle-shaped body precursor 106. The needle-shaped body precursor 106 is produced by a method using a publicly known micro-fabrication technology. As the publicly known micro-fabrication technology, for example, following methods can be used.

(1) Manufacturing method using micromachining such as grinding or cutting to the base portion.

(2) Manufacturing method using a micro-fabrication technology such as lithography or etching.

(3) Method using transfer-molding where a needle-shaped body original plate produced by the above-mentioned known method is transferred to form a needle-shaped body precursor.

According to the present embodiment, a silicon substrate 101 shown in FIG. 1(a) is ground such that a ground groove 102 is formed, with a portion for a base portion 104 being remained as shown in FIG. 1(b). FIGS. 1(a)-1(f) and 1(g)-1(l) are cross sectional views in which the silicon substrate 101 is cut off along the longitudinal direction of the ground groove 102. As shown in FIG. 1(c), the needle-shaped body precursor 106 includes a needle-shaped portion 105 and the base portion 104 that supports the needle-shaped portion 105. The needle-shaped portion 105 is formed by grinding the silicon substrate 101.

A substrate used for producing the needle-shaped body precursor 106 is appropriately selected according to a processing method. The substrate is not limited to the silicon substrate 101. For example, a substrate can be made of carbon, ceramics, quartz, metal, resin or the like. In particular, since silicon or quartz can be hydrophilic or hydrophobic depending on how the native oxide film thereof is processed, surface energy can be favorably controlled. These characteristics are favorable for a substrate material to form a curved surface portion of the present embodiment by dropping a curved surface material, which will be described later.

According to the present embodiment, shape and dimension of the base portion 104 and the needle-shaped body precursor 106 are appropriately designed and determined. Specifically, the needle-shaped portion 105 may have a shape of a cone, a pyramid, a column, a rectangular column, a conic trapezoid, a pyramidal trapezoid or the like. However, according to the present embodiment, since the needle-shaped portion 105 and the base portion 104 are joined such that the side surface of the needle-shaped portion 105 forms an acute angle with respect to an upper surface 104a of the base portion 104, the joint portion preferably has flatness. Accordingly, the needle-shaped portion 105 preferably has a polygonal shape at least a portion to be joined to (portion to contact with) the base portion 104. As the polygonal shape, for example, a pyramid, a rectangular column, a pyramidal trapezoid or the like is preferably be used.

The needle-shaped body according to the present embodiment may have a shape where a plurality of needle-shaped portions 105 stands on the base portion 104. In the case where the needle-shaped body has a shape (arrayed shape) where a plurality of needle-shaped portions 105 stands on the base portion 104, lengths of the respective needle-shaped portions 105 may be or may not be the same among the needle-shaped portions 105.

In the case where the lengths of the respective needle-shaped portions 105 are not the same, for example, the following effects can be obtained:

(1) Only a portion in an outer periphery of the array can have long needle-shaped body units, thereby enabling favorable contact with the curbed surface.

(2) Only a portion in an outer periphery of the array can have short needle-shaped body units, thereby enhancing the mechanical strength of the needle-shaped portions 105 in the outer peripheral portion which is likely to be broken. A pitch dimension which is a distance between the needle-shaped portions 105 can be appropriately designed and determined, depending on the specification thereof.

The needle-shaped portion 105 is preferably sufficiently thin to perforate the skin and has a length not reaching a nerve layer. Specifically, the diameter of the needle-shaped portion 105 preferably ranges from approximately several μm to several hundreds μm, and the length of the needle-shaped portion 105 preferably ranges from approximately several μm to several hundreds μm.

Specifically, when the length of perforation is required to be sufficient for passing through the stratum corneum but restricted not to reach the nerve layer, the required length of the needle-shaped portion 105 specifically preferably ranges, from 200 μm to 700 μm, and more preferably from 200 μm to 500 μm. Furthermore, the length is preferably within a range approximately from 200 μm to 300 μm.

In the case where the depth of perforation by the needle-shaped portion 105 is required to be sufficient for passing through the stratum corneum but restricted not to reach the nerve layer, an object to be delivered can be delivered to a position deeper than the stratum corneum.

In particular, when perforation is restricted within the stratum corneum, the required length of the needle-shaped portion 105 specifically preferably ranges, from 30 μm to 300 μm, and more preferably from 30 μm to 250 μm. Furthermore, the length is preferably within a range approximately from 30 μm to 40 μm.

In the case where the perforation depth by the needle-shaped portion 105 is restricted within the stratum corneum, an object to be delivered can be retained in the stratum corneum. Since the stratum corneum is constantly newly produced by metabolism, the object to be delivered in the stratum corneum is discharged outside the body with time. Therefore, the present embodiment can be favorably used for removing drugs in a short period of time, for maintaining a make-up state for a short period time, or the like.

Step of Producing Needle-Shaped Body Original Plate

Next, in the present embodiment, a curved surface portion 110 having a convex shape is formed on at least a part of a joint portion 107 between the base portion 104 and the needle-shaped portion 105 of the needle-shaped body precursor 106 so as to produce a needle-shaped body original plate 111. More specifically, the curved surface portion 110 having a convex shape is formed on at least a part of apex portions of the polygon included in the needle-shaped portion 105 located at the joint portion 107 which is a boundary portion between the base portion 104 and the needle-shaped portion 105 of the needle-shaped body precursor 106, thereby producing the needle-shaped original plate 111.

As a method of forming the curved surface portion 110 on the needle-shaped body precursor 106, a dispenser method is mainly used such that a small amount of a material for forming the curved surface portion is dropped onto at least a part of a joint portion 107 between the base portion 104 and the needle-shaped portion 105 of the needle-shaped body precursor 106.

Figure 1D:
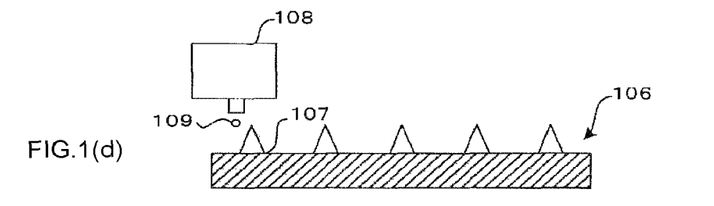

FIGS. 1(d) to 1(g) are manufacturing process diagrams illustrating a method of producing the needle-shaped body original plate 111. According to the present embodiment, as shown in FIG. 1(d), a dispenser 108 is used to drop a curved surface portion-forming material 109 onto the joint portion 107 between the base portion 104 and the needle-shaped portion 105 of the needle-shaped body precursor 106.

Figure 1E:
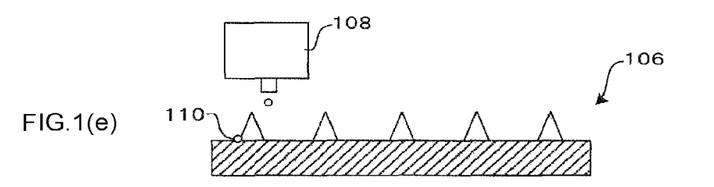
Figure 1F:
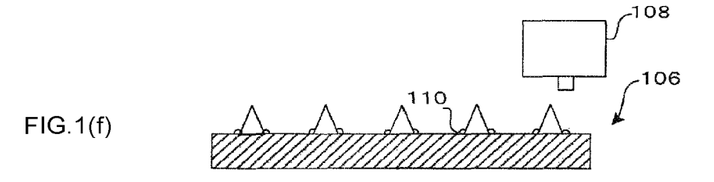

As shown in FIGS. 1(e) and 1(f), the curved surface portion-forming material 109 is dropped onto all the joint portions 107 on the base portion 104, residing between the base portion 104 and the needle-shaped portion 105.

It should be noted that the curved surface-forming material 109 may be dropped on a part of the periphery of the joint portion 107 between the base portion 104 and the needle-shaped portion 105 or may be dropped on the entire surface of the joint portion 107.

The dispenser 108 is preferably provided with a pressurization mechanism of a mechanical conversion type or a thermal conversion type, having a discharge resolution of several pico liter order by use of a nozzle diameter of several 10 μm order. Specifically, for the dispenser 108, a jet-type dispenser using compressed air or the like, an ink-jet type dispenser using a piezoelectric device or the like, a needle-type dispenser using a movable mechanism in height direction can be used.

The material for the curved surface-forming material 109 is not particularly limited as long as the dispenser 108 can drop the material 109. The curved surface-forming material 109 may be a natural polymer material such as polysaccharide, protein and nucleic acid, or a synthetic polymer such as polyolefin or a vinyl-polymer.

In the present embodiment, a solvent may be appropriately added based on the polarity of the curved surface-forming material 109. Generally, it is known that a polar material easily disperses in a polar solvent (water system or the like), and a non-polar material easily disperses in a non-polar solvent (solvent based).

The polarity material includes, for example, ketons such as acetone, methyl ethyl ketone (MEK), methyl isobutyl ketone (MIBK), alcohols such as methyl alcohol, ethyl alcohol and 2-propanol, esters such as ethyl acetate and n-butyl acetate, or pure water or the like.

The non-polarity solvent includes, for example, aromatic hydrocarbons such as isooctane, cyclohexane and isophorone, and aliphatic hydrocarbons such as toluene, xylene, mesitylene, 1,2,3,4-tetrahydronaphthalene (tetralin), n-hexane and n-decane.

In the present embodiment, a material which is semi-solidified by a gelatinizing effect after being dropped may be added to the curved surface-forming material 109. By gelatinizing the curved surface-forming material 109, molding defects caused by a surface tension of the curved surface portion 110 are suppressed. Hence, gelatinization is advantageous to appropriately perform a transfer molding process by use of a resin plate, which will be described later. In the case where the curved surface-forming material 109 is gelatinized, the curved surface-forming material 109 dispersed into various solvents is mixed with a gelatinizer.

The gelatinizer to gelatinize the curved surface-forming material 109 is not particularly limited. However, the gelatinizer that can be used includes gelatin, pectin agar, carrageenan, carboxymethylcellulose sodium, xanthan gum, guar gum or the like, for example.

The viscosity of the curved surface portion forming material 109 is not particularly limited as long as the viscosity falls within a range where various dispensers 108 are applicable. The gelatinized curved surface-forming material 109 is preferably viscous and fluidized when coated. The gelatinized curved surface-forming material 109 is heated in advance coated, whereby fluidity can be provided to the gelatinized curved surface-forming material 109 so that the curved surface portion 110 can favorably be formed. The gelatinized curved surface-forming material 109 is gelatinized again when cooled after being coated.

When forming the curved surface portion 110 having a convex shape, wettability has to be controlled between the curved surface portion forming material 109 and the needle-shaped body original plate 111. Prior to forming the curved surface portion 110, a surface treatment may be applied to the needle-shaped body precursor 106. A water-repellent treatment can be used as a surface treatment, whereby a contact area of the droplet of the curved surface-forming material 109 can be made small. Hence, the size of the curved surface portion 110 can be controlled. The water-repellent treatment includes, for example, a treatment using a silane coupling agent such as HMDS (Hexamethyldisilazane), water-repellent plating containing fluorine particles, a treatment using a micro-fabrication technology to form fine unevenness, metal plating, or the like.

In the case where the wettability of the curved surface-forming material 109 is required to be improved, a hydrophilic treatment may be performed as needed depending on desired surface properties. Methods of the hydrophilic treatment include, for example, ozone irradiation, electromagnetic radiation using ultraviolet rays, X-rays or the like, electron beam irradiation, plasma irradiation, addition of characteristics reforming substance to the surface, addition of photocatalyst to the surface, or the like.

It should be noted that the 'convex shape' which is the shape of the curved surface portion 110 represents that the cross-sectional shape of the curved surface portion 110 taken along a thickness direction of the base portion 104 is a convex shape.

Step of Producing Resin Plate

Figure 1G:
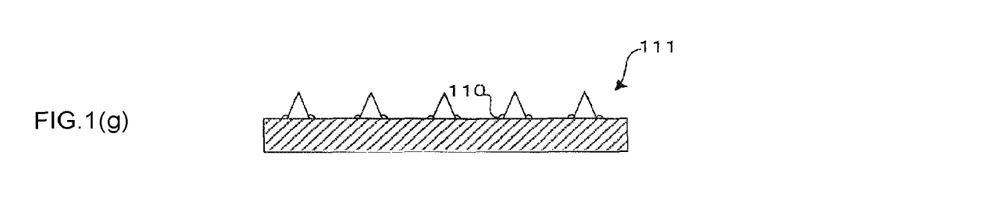
FIG. 1(g)-1(l) are process charts subsequent to FIG. 1(f), showing the manufacturing method of the needle-shaped body according to an embodiment of the present invention.
Figure 1H:
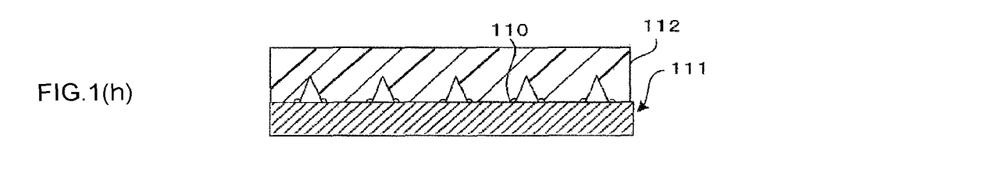
Figure 1I:
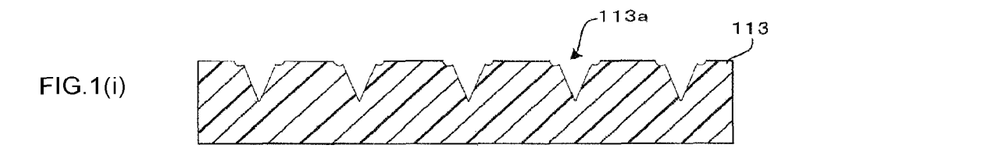

FIGS. 1(h) and 1(i) are cross-sectional views showing a step of producing a resin plate 113. First, according to the present embodiment, as shown in FIG. 1(h), a resin plate material 112 is filled into the needle-shaped original plate 111. Next, a resin plate 113 is produced by transfer-molding using the needle-shaped original plate 111. The resin plate 113 includes a concave pattern 113a corresponding to the shape of the needle-shaped portion 105 of the needle-shaped original plate 111 and the curved surface portion 110. FIG. 1(i) illustrates the resin plate 113. According to the present embodiment, the resin plate material 112 is not specifically limited, but is selected considering conformability to shape, transfer-molding properties, plate durability and peelability, so as to serve as the resin plate 113. Specifically, the resin plate 113 is made of a thermosetting resin such as a silicon resin having high flexibility or an epoxy resin. However, the material of the resin plate 113 is not limited to the thermosetting resin. For example, a thermoplastic resin or an ionizing radiation curable resin can be used for the resin plate 113.

The resin plate material 112 is preferably a biocompatible material. When the resin plate material 112 is produced using a biocompatible material, adverse effect to human body is unlikely to happen, if the needle-shaped portion 105 with a part of the resin plate material being adhered thereto is broken when puncturing the skin, for example, causing bending, chipping or the like. In particular, according to the needle-shaped body 115 of the present embodiment, a fine projection portion of the needle-shaped portion 105 stays in the skin, being engaged thereto, and thus the needle-shaped portion 105 is likely to remain inside the body. As a result, good effect can be obtained by using a biocompatible material.

The resin plate 113 can be produced appropriately using a known pattern transfer method depending on the resin plate material 112. For example, when thermosetting resin (e.g., silicon resin, epoxy resin or the like) is used for the resin plate material 112, the resin plate material 112 is filled in the needle-shaped body original plate 111, followed by curing the resin plate material 112, and then by peeling the resin plate material 112 from the needle-shaped original plate 111, thereby producing the resin plate 113. Since some types of silicon can be cured at room temperature, such a silicon may be used for the resin plate material 112 to produce the resin plate 113 at room temperature.

Methods for filling the material of the resin plate 113 into the needle-shaped original plate 111 include, for example, imprinting, hot embossing, injection molding, extrusion, casting and the like. In the present embodiment, thickness of the resin plate material 112 to be filled in is not specifically limited, but an appropriate thickness can be selected to form the needle-shaped body 115.

As a method of peeling the resin plate 113 from the needle-shaped original plate 111, for example, (1) peeling by using physical peeling force, (2) selective etching, or the like can be used.

Step of Producing Needle-Shaped Body

Next, a method of producing the needle-shaped body 115 with a transfer molding using the resin plate 113 will be described. The needle-shaped body 115 includes a needle-shaped portion (transfer needle-shaped portion) and a curved surface portion (transferred curved surface portion).

Figure 1J:
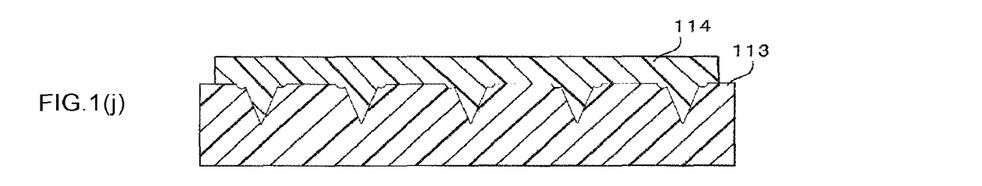
Figures 1K, 1L:
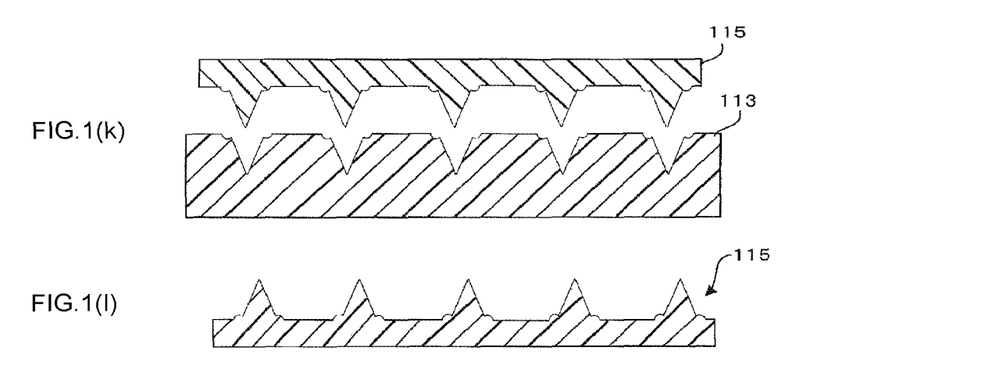

FIGS. 1(j) to 1(l) are process charts illustrating a method of producing a needle-shaped body 115 according to the present embodiment. According to the present embodiment, as shown in FIG. 1(j), a needle-shaped material 114 is filled in the resin plate 113. As shown in FIG. 1(k), after the needle-shaped body material 114 filled in the resin plate 113 has solidified, the solidified needle-shaped material 114 (needle-shaped body 115) is peeled from the resin plate 113. FIG. 1(l) illustrates the needle-shaped body 115.

In the present embodiment, the needle-shaped material 114 is not specifically limited. However, a biocompatible material including a medical silicone resin, maltose, polylactate, dextran, carbohydrate or the like can be used. In the present embodiment, the needle-shaped body 115 applicable to the human body can be formed by using such a material.

Such a biocompatible material is used for the needle-shaped body 115 to obtain the effect that it is harmless to human body if the needle-shaped portion is broken and remained inside the body. Also, as the needle-shaped body material 114, an epoxy resin, a polyamide resin, a phenol resin or the like can be used other than biocompatible materials.

A method of filling the needle-shaped body material 114 is not particularly limited. However, for example, hot pressing, hot embossing, injection molding, extrusion or casting is preferably used.

According to the present embodiment, the needle-shaped body 115 is removed from the resin plate 113 after the steps described above to obtain the needle-shaped body 115. In other words, a needle-shaped body 115 provided with a needle-shaped portion and a curved surface portion is obtained, where shapes of the needle-shaped portion 105 and the curved surface portion 110 are transferred thereto by transfer molding using the resin plate 113.

The peeling method is not specifically limited, but a method that can be used is a physical peeling method. Specifically, in the physical peeling method, a peeling claw made of metal such as SUS304 or SUS440 is inserted between the resin plate 113 and the needle-shaped body 115, or brought into contact with an end portion of the base portion 104 of the needle-shaped body 115 to hold the needle-shaped body 115, whereby the resin plate 113 is peeled from the needle-shaped body 115.

An outline of the manufacturing method of the needle-shaped body 115 according to the present embodiment has so far been described. The present embodiment is not limited to the above-described examples, and other methods applicable to respective manufacturing processes can be used.

Structure of Needle-Shaped Body

Figure 2A:
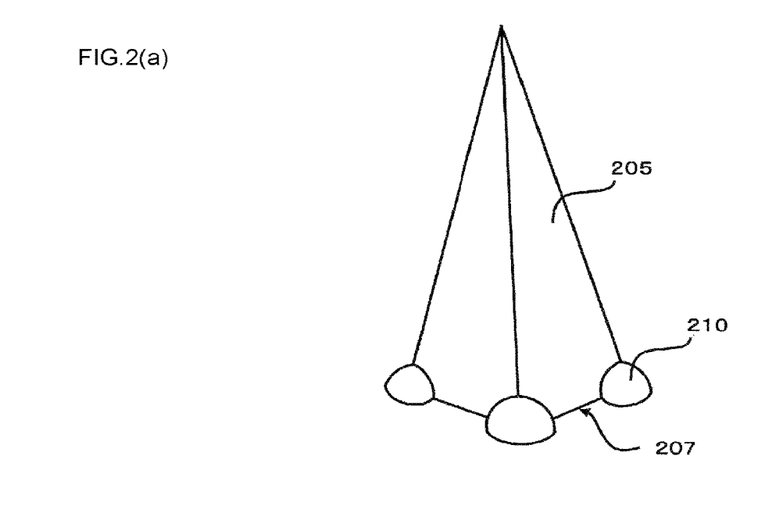
FIGS. 2(a) and 2(b) are perspective views showing a structure of a needle-shaped body according to an embodiment of the present invention.
Figure 2B:
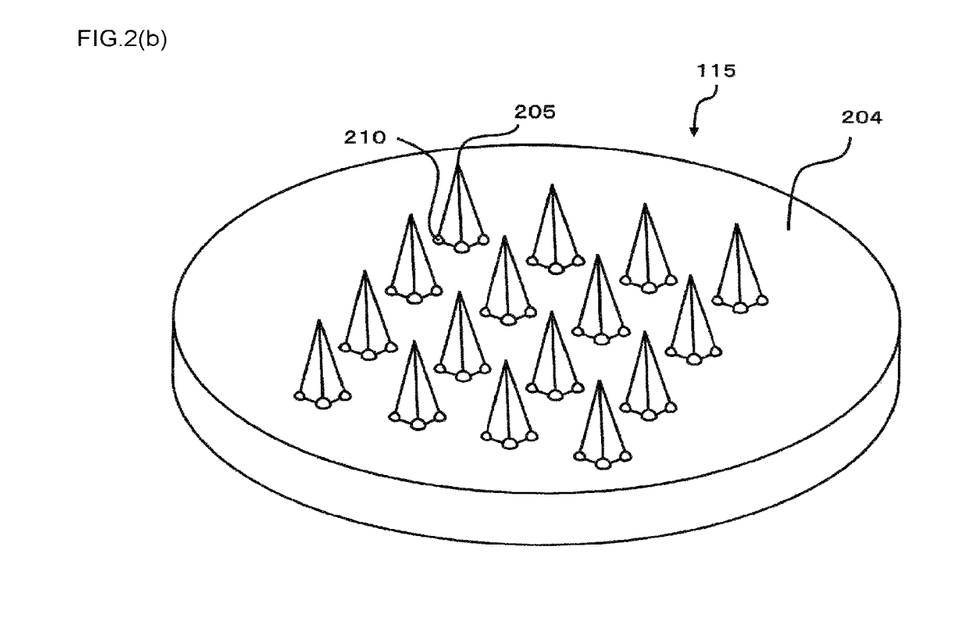

FIGS. 2(a) and 2(b) are enlarged perspective views showing a part of the needle-shaped body 115 (single needle-shaped portion 205) manufactured with the method described above. As shown in FIGS. 2(a) and 2(b), the needle-shaped body 115 produced by the manufacturing method of the present embodiment is provided with a base portion 204 and a needle-shaped portion (transferred needle-shaped portion) 205. Further, a curved surface portion (transferred curved surface portion) 210 having a convex shape is provided at at least a part of a joint portion 207 between the base portion 204 and the needle-shaped portion 205. Further, according to the present embodiment, a joint portion of the needle-shaped portion 205 to the base portion 204 has a polygonal shape (e.g., pyramid shape), in which the convex-shaped curved surface portion 210 is selectively formed on an apex portion of the polygon in the joint portion 207 between the base portion 204 and the needle-shaped portion 205.

Since the convex-shaped curved surface portion 210 according to the present embodiment reinforces the needle-shaped portion 205 and the base portion 204 when the needle-shaped body 115 punctures the skin, the needle-shaped portion 205 is unlikely to be broken. Also, according to the present embodiment, the size of the curved surface portion 210 is controlled, whereby depth of puncture into the skin can be controlled.

Figure 3:
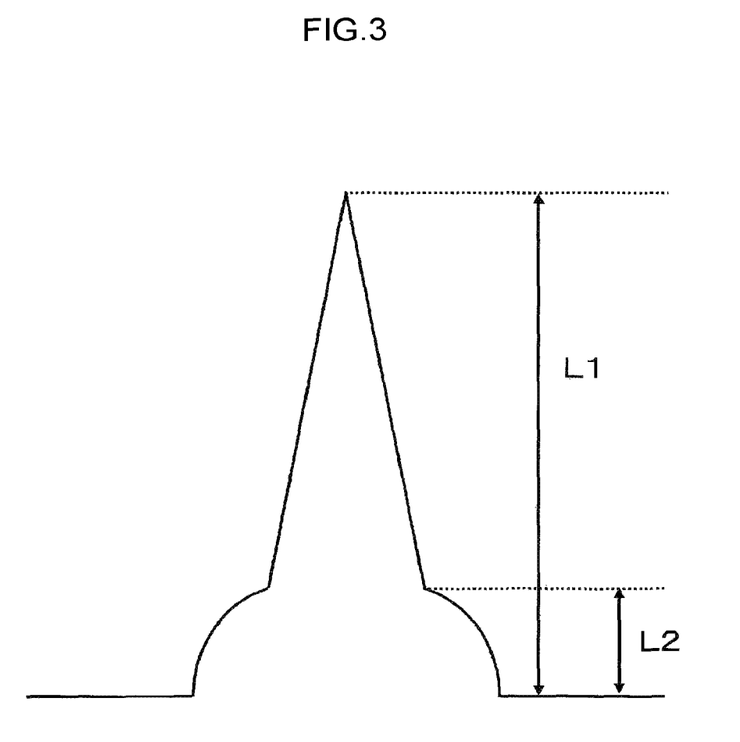
FIG. 3 is a cross-sectional view showing a structure of a needle-shaped body according to an embodiment of the present invention.

FIG. 3 is a schematic cross-sectional view of the needle-shaped body 115 according to the present embodiment. More specifically, FIG. 3 is a schematic cross-sectional view of the needle-shaped portion 205 and the curved surface portion 210 shown in FIG. 2 (a) taken along the left-right direction of FIG. 2 (a). Height L1 from a surface of the base portion 204 to an apex portion of the needle-shaped portion 205 is preferably in a range from 50 μm to 2000 μm, inclusive. Further, the height L2 from the surface of the base portion 204 to the apex portion of the curved surface portion 210 (highest portion) is preferably in a range from L1×0.05 to L1×0.5, inclusive, with reference to Height L1 of the needle-shaped portion 205.

Structure of Needle-Shaped Body According to Modification

Figure 4A:
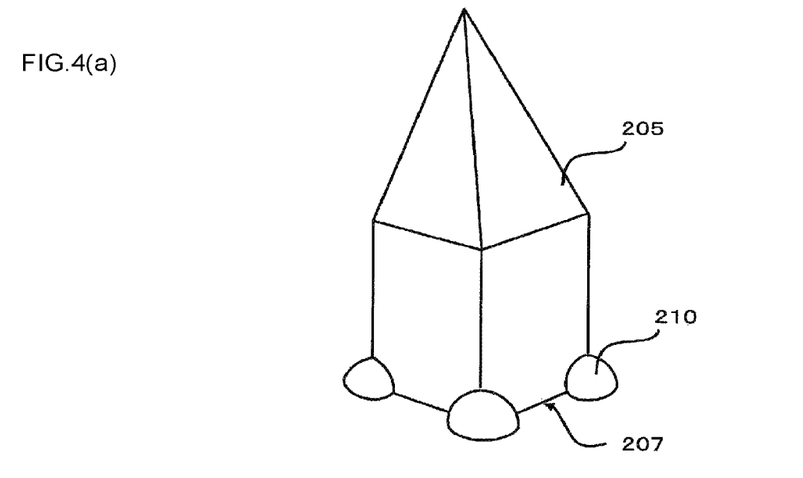
FIGS. 4(a) and 4(b) are perspective views showing a structure of a needle-shaped body according to a first modification of the present invention.
Figure 4B:
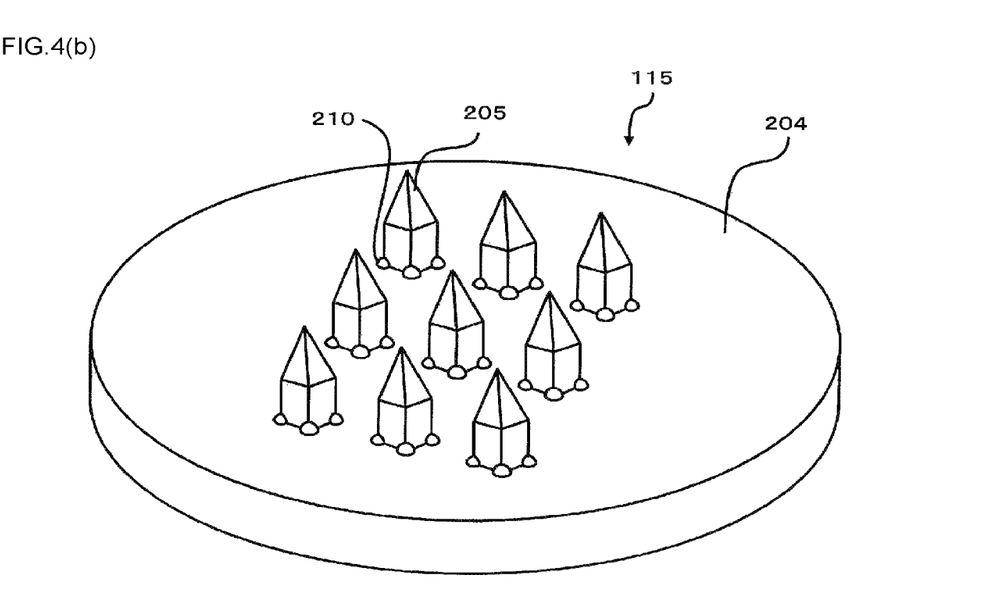

FIGS. 4(a) and 4(b) are perspective views (first modification) of a needle-shaped body 115 according to the present embodiment. The needle-shaped body 115 shown in FIG. 4(b) includes the needle-shaped portion 205 with a shape in which a quadrangular prism and a quadrangular pyramid are connected in this order from the base portion 204. It should be noted that the shape of the needle-shaped body 115 can be, for example, a polygonal pyramid shape such as of a trigonal pyramid, a quadrangular pyramid, a pentagonal pyramid or a hexagonal pyramid. As shown in FIGS. 4(a) and 4(b), a polygonal pyramid shape and a polygonal prism shape may be combined. According to the present embodiment, a polygonal pyramid shape and a polygonal prism shape are combined to form respective shapes.

Since the rest of the configuration is the same as that of the above-described embodiments, detailed description is omitted.

Figure 5A:
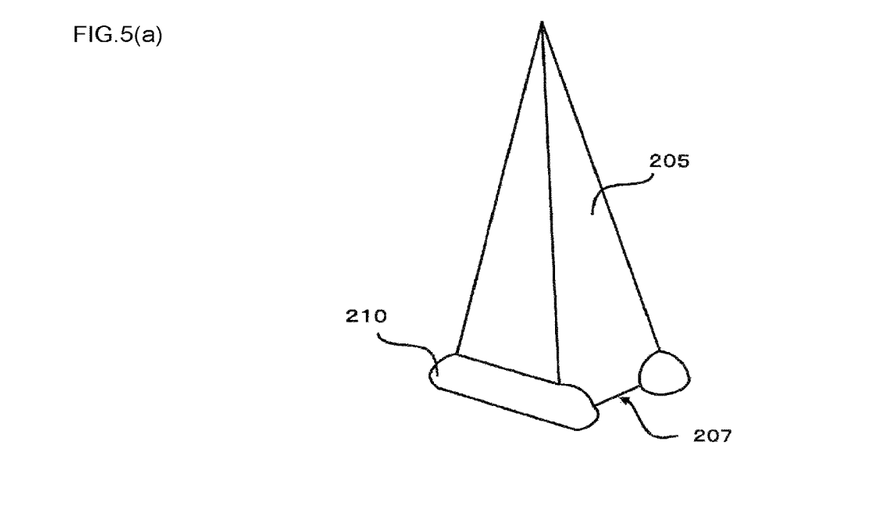
FIGS. 5(a) and 5(b) are perspective views showing a structure of a needle-shaped body according to a second modification of the present invention.
Figure 5B:
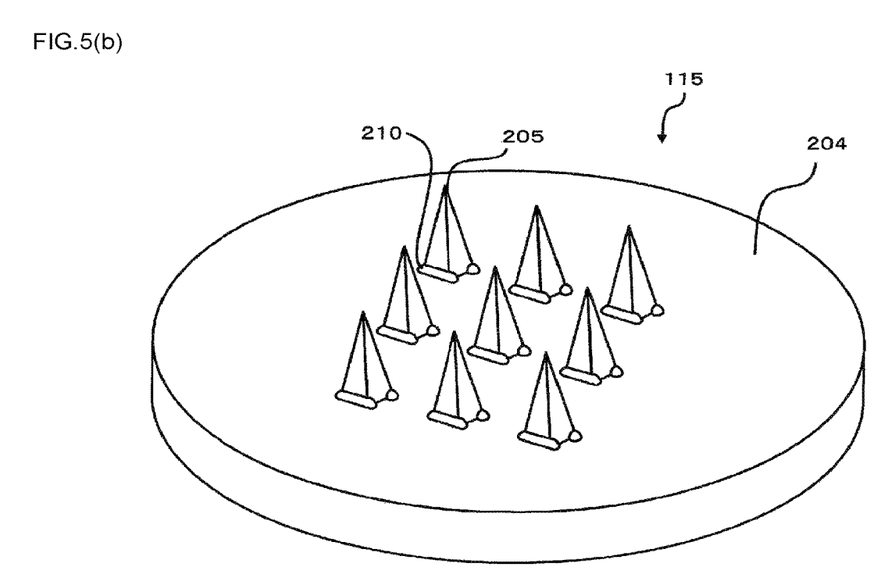

FIGS. 5(a) and 5(b) are perspective views (second modification) of a needle-shaped body 115 according to the present embodiment. In the needle-shaped body 115 shown in FIG. 5(b), a curved surface portion 210 is formed across two apex portions among four apex portions of the pyramid shape on the joint portion 207 between the needle-shaped portion 205 having a quadrangular shape and the base portion 204.

For other portions, since configurations are the same as that of the above-described embodiments, detailed description is omitted.

Figure 6A:
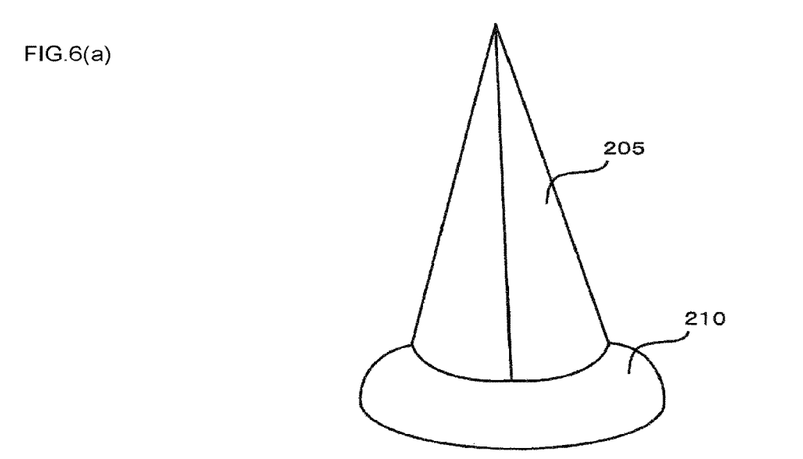
FIGS. 6(a) and 6(b) are perspective views showing a structure of a needle-shaped body according to a third modification of the present invention.
Figure 6B:
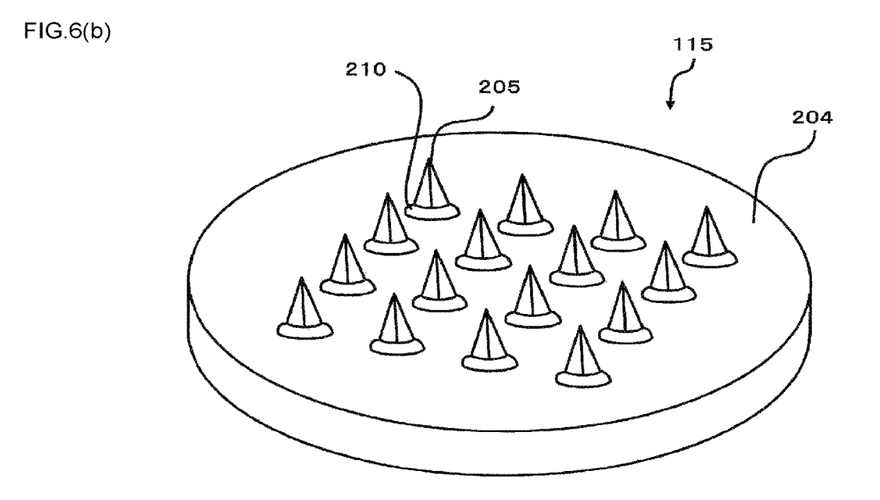

FIGS. 6(a) and 6(b) are perspective views (third modification) of a needle-shaped body 115 according to the present embodiment. In the needle-shaped body 115 shown in FIG. 6(b), a curved surface portion 210 is formed throughout the outer periphery of the pyramid on the joint portion 207 between the needle-shaped portion 205 having a quadrangular shape and the base portion 204.

For other portions, since configurations are the same as that of the above-described embodiments, detailed description is omitted.

Figure 7A:
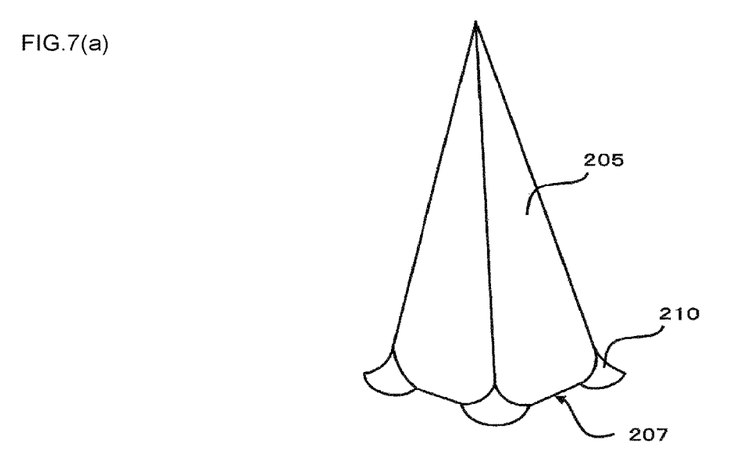
FIGS. 7(a) and 7(b) are perspective views showing a structure of a needle-shaped body according to a fourth modification of the present invention.
Figure 7B:
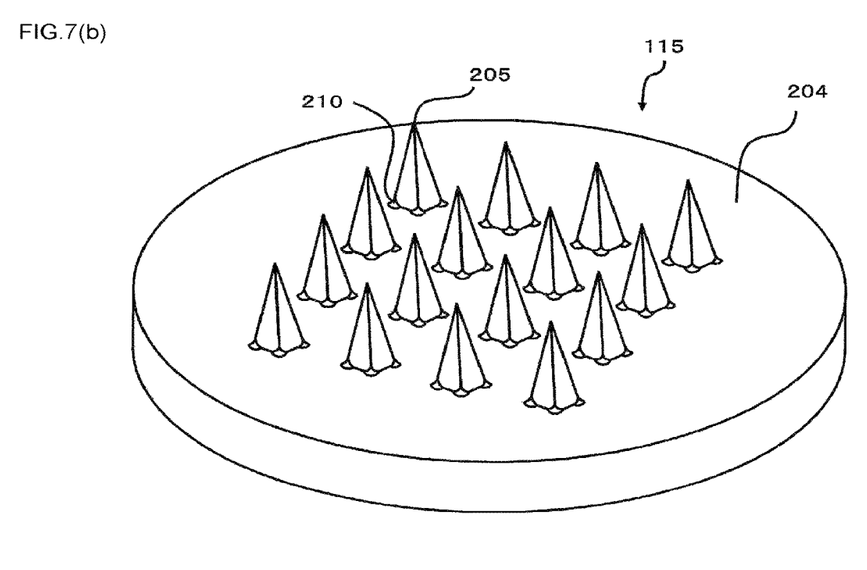

FIGS. 7(a) and 7(b) are perspective views (fourth modification) of a needle-shaped body 115 according to the present embodiment. In the needle-shaped body 115 shown in FIG. 7(b), the curved surface portion 210 is not formed into a convex shape but formed into a concave shape. The curved surface portion 210 can be formed into a concave shape shown in FIGS. 7(a) and 7(b). However, taking into consideration of the plate durability, the curved surface portion 210 may be formed into a convex shape rather than a concave shape, so as to obtain significant effects.

It should be noted that the concave shape refers to that the cross section of the curved surface portion 210 taken along a thickness direction of the base portion 204 is in a concave shape. For other portions, since configurations are the same as that of the above-described embodiments, detailed description is omitted.

According to the present embodiment described above, the resin plate 113 is unlikely to be damaged when the needle-shaped body 115 is peeled from the resin plate 113 in the transfer molding, due to the effects of the curved surface portion 210 having a convex shape formed on the joint portion 207 between the base portion 204 and the needle-shaped portion 205. As a result, without impairing the shape of the needle-shaped portion 205 which contributes to skin puncturing properties, productivity of the needle-shaped body 115 can be improved.

The needle-shaped body 115 according to the present embodiment may be provided with a through hole (not shown) used for discharging a liquid medicine into the skin. More specifically, the needle-shaped body 115 according to the present embodiment may be provided with a through hole penetrating through both the base portion 204 and the needle-shaped portion 205. The through hole may penetrate a side surface portion of the needle-shaped portion 205.

EXAMPLES

Hereinafter, an example of the present embodiment will be described with reference to FIGS. 1(a)-1(f) and 1(g)-1(l) referred to above.

First, as shown in FIG. 1(a), the inventor of the present invention prepared a silicon substrate 101 having a square shape of which the one side is 50 mm and the thickness was 2 mm, ground a surface of the silicon substrate 101 with a depth of 300 μm by rotating a grinding blade so as to form a ground groove 102 having a length of 50 mm. The width of the upper opening of the ground groove 102 was about 418 μm and the depth was 300 μm.

The ground groove 102 had a side wall surface inclination corresponding to an inclination of an inclined surface formed at a tip end of the grinding blade. According to the present example, the angle formed between a parallel surface of the silicon substrate 101 and a side wall surface of the ground groove 102 was 110°. Six ground grooves 102 were formed. As shown in FIG. 1(b), a silicon substrate 103 in the process of being ground and having an approximately triangular cross section was obtained.

Next, the silicon substrate 103 in the process of being ground was rotated by 90° with respect to a direction in which the ground groove 102 extended (longitudinal direction), and ground again with the same condition as that of the forming process of the ground groove 102. As a result, the needle-shaped portions 105 each having a quadrangular pyramid shape were formed in an array of 5 rows and 5 columns on the base portion 104. The tip end angle of each needle-shaped portion 105 was 40°, the height was 300 μm, and the width of one side in the bottom surface thereof was approximately 231 μm.

Also, a water-repellent treatment was applied to the surface of the silicon substrate 103 with hexamethyldisilazane. After the water-repellent treatment, the contact angle of the silicon substrate 103 to the water was 120° and water-repellent properties were confirmed.

As a result, a needle-shaped body precursor 106 was obtained as shown in FIG. 1(c).

Next, using a dispenser 108, the curved surface-forming material 109 was dropped, as shown in FIG. 1(d), onto the joint portion 107, aiming at a surface near each apex portion of the square cross section, where the base portion 104 was bonded to the needle-shaped portion 105 of the needle-shaped precursor 106. For the dispenser 108, an MD-K-140 (nozzle-diameter 50 μm) manufactured by microdrop Technologies was used.

For the curved surface-forming material 109, a solution was used, which was a mixture of polyethylene glycol (weight average molecular weight 1000) manufactured by Kanto Chemical Co., Inc and pure water with a weight ratio 1:1. The curved surface-forming material 109 was heated by setting the nozzle temperature of the dispenser 108 to 40 C.°. As a result, the curved surface-forming material 109 having a diameter of about 50 μm was discharged.

As shown in FIG. 1(e), the curved surface-forming material 109 was discharged while the position of the dispenser 108 was changed with respect to the joint portion 107. As a result, the curved surface-forming material 109 reached the joint portion 107 to form the curved surface portion 110 having a thickness of 20 μm and a diameter of approximately 30 μm at a solidified and dried portion under a normal environment.

Further, as a result of discharging, drying and solidifying the curved surface-forming material 109, the curved surface portions 110 were formed on all of the joint portions 107. As a result, as shown in FIG. 1(g), the needle-shaped original plate 111 was produced.

Subsequently, as shown FIG. 1(h), the resin plate material 112 was filled in the needle-shaped body original plate 111. For the resin plate material 112, a thermosetting silicone resin (KE-1417 (product name)) manufactured by Shin-Etsu Chemical Co., Ltd was used. The resin plate material 112 was cured at room temperature and released, whereby a resin plate 113 having a square shape of which the one side was 50 mm and the thickness was 10 mm, was produced as shown in FIG. 1(i).

Next, as shown in FIG. 1(j), the needle-shaped body material 114 was filled in the resin plate 113 by hot pressing. Polyglycolic acid Kuredux 100E35 (product name) manufactured by Kureha Corporation was used for the needle-shaped body material 114.

Lastly, as shown in FIG. 1(k), the needle-shaped body material 114 was released after being sufficiently cooled in the resin plate 113. As a result, as shown in FIG. 1(l), the needle-shaped body 115 according to the present example was produced.

Comparative Example

As a comparative example, a needle shaped body without the curved surface portion 110 was produced in the above-described example.

Specifically, similar to the above-described example, a silicon substrate having a square shape of which the one side was 50 mm and the thickness was 2 mm, was prepared, and a surface of the silicon substrate was ground with a depth of 300 μm by rotating a grinding blade so as to form a ground groove having a length of 50 mm. The width of the upper opening of the ground groove was about 418 μm and the depth was 300 μm.

The ground groove had a side wall surface inclination corresponding to an inclination of an inclined surface formed at a tip end of the grinding blade. According to the comparative example, the angle formed between a parallel surface of the silicon substrate and a side wall surface of the ground groove was 110°. Six ground grooves were formed. A silicon substrate in the process of being ground and having an approximately triangular cross section was obtained.

Next, similar to the above-described example, the silicon substrate in the process of being ground was rotated by 90° with respect to a direction in which the ground groove extended (longitudinal direction), and grinded again with the same condition as that of the forming process of the ground groove. As a result, the needle-shaped portion having a quadrangular pyramid shape was formed in an array of 5 rows and 5 columns on the base portion. The tip end angle of the needle-shaped portion was 40°, the height was 300 μm, and the width of one side in the bottom surface was approximately 231 μm. Thus, a needle-shaped body original plate according to the comparative example was produced.

Subsequently, similar to that of the above-described example, a resin plate material was filled onto the needle-shaped body original plate. For the resin plate material, thermosetting silicone resin (KE-1417 (product name)) manufactured by Shin-Etsu Chemical Co., Ltd was used.

The resin plate material was cured at room temperature and released, whereby a resin plate having a square shape of which the one side is 50 mm and a thickness of 10 mm was produced.

Next, a needle-shaped body material was filled onto the obtained resin plate by using a thermal press method. Polyglycolic acid Kuredux100E35 (product name) manufactured by Kureha Corporation was used for the needle-shaped body material.

Lastly, the needle-shaped body material was released after being sufficiently cooled in the resin plate. Thus, a needle-shaped body according to the comparative example, i.e., a needle-shaped body without the curved surface portion 110 was produced.

(Comparison of Plate Durability)

100 pcs of needle-shaped body 115 made of polyglycolic acid obtained in the example were repeatedly produced by continuously using the same resin plate 113. After producing the 100 pcs of the needle-shaped body 115, the surface of the resin plate 113 used for the production was observed with a stereoscopic microscope.

On the other hand, similar to the example, 100 pcs needle-shaped body made of polyglycolic acid obtained in the comparative example were repeatedly produced by continuously using the same resin plate. After producing the 100 pcs of the needle-shaped bodies, similar to the example case, the surface of the resin plate used for the production was observed with a stereoscopic microscope.

Figure 8A:
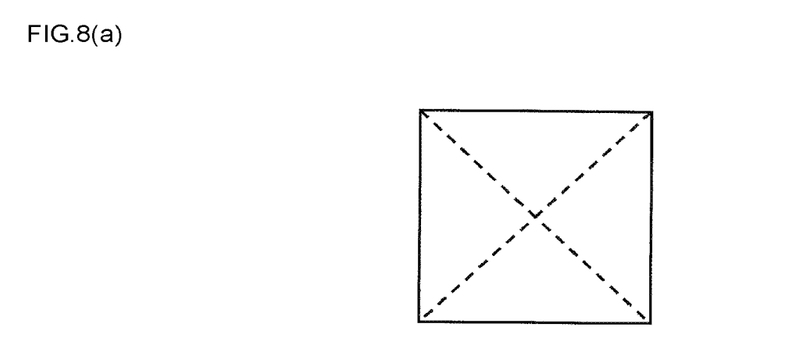
FIGS. 8(a) and 8(b) are plan views showing an observation result of a surface of a resin plate used in a comparative example of the present invention.
Figure 8B:
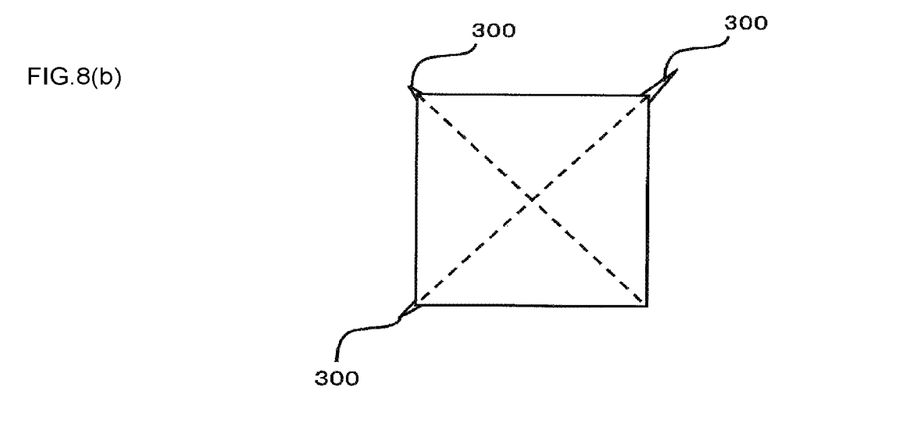

As a result of the observation, cracks (clefts) were confirmed on the surface of the resin plate according to the comparative example. The crack was caused at an apex portion of the quadrangular pyramid of the needle-shaped body of the resin plate. On the other hand, no crack was observed on a surface of the resin plate 113 of the example. FIGS. 8(a) and 8(b) are explanatory diagrams showing the observation result of the surface of the resin plate used in the comparative example by use of the stereoscopic microscope. FIG. 8 (a) is a schematic diagram showing the observation result of the resin plate surface through a photograph taken by the stereoscopic microscope before the needle-shaped body was formed. FIG. 8(b) is a schematic diagram showing the observation result of the resin plate surface through a photograph taken by the stereoscopic microscope after forming 100 pcs of needle-shaped body. In FIGS. 8 (a) and (b), center squares each show a concave pattern corresponding to the needle-shaped portion of the needle-shaped body. As shown in FIG. 8 (b), in the resin plate used for the comparative example, cracks (clefts) 300 were confirmed at concave portions corresponding to the apex portions of the quadrangular pyramid of the needle-shaped body. Again, cracks that were confirmed in the comparative example were not observed in the resin plate 113 of the example even after forming 100 pcs of needle-shaped bodies.

As will be understood from the above, according to the manufacturing method of the needle-shaped body 115 of the example, durability of the resin plate 113 is high so that the resin plate 113 is not required to be replaced often, comparing with the manufacturing method of the needle-shaped body of the comparative example. Therefore, it has been found that the manufacturing method of the needle-shaped body 115 of the example has high productivity.

The present invention has been described as set forth above with reference to a specific embodiment. However, the invention is not limited by the description. Referring to the description of the present invention, it is apparent for the person having ordinary skill in the art to reach various modifications of the disclosed embodiment and also reach other embodiments of the present invention.

Accordingly, it should be understood that the scope of claims encompasses modifications and embodiments included in the scope and the spirit of the present invention.

The manufacturing method of a needle-shaped body and the needle-shaped body according to the above-described embodiment can solve the problems to be solved by the present invention. Hereinafter, the above-mentioned problems to be solved by the present invention will be described in detail.

Currently, there is a percutaneous absorption method as a method of administering medicine into a body by perforating the medicine from above the skin. The percutaneous absorption method is capable of easily administering a medicine to a person in need of administration without pain.

However, it is difficult for some medicines to be administered by using the percutaneous absorption method. As a method of effectively absorbing a medicine, which is difficult to be administered into a body, micro-order fine needle-shaped body (microneedle) is used to perforate the skin so as to directly administer the medicine into the skin. According to the method of administering a medicine into the skin by using the needle-shaped body, the medicine can be easily administered into the skin without using a conventional injection device. It should be noted that such a technique of the needle-shaped body is known as disclosed in PTL 1, for example.

The needle-shaped body has a fine needle-shaped portion that perforates the skin and a base that supports the needle-shaped body. The needle-shaped portion requires to be sufficiently thin have a tip end angle sufficient for perforating the skin, and have a sufficient length for permeating a liquid medicine into the skin. The diameter of the needle-shaped portion preferably ranges from several μm to several hundred of μm, and the length of the needle-shaped portion is preferably sufficiently large to penetrate the stratum corneum which is the outermost layer of the skin but not to reach the nerve layer. Specifically, the needle-shaped portion preferably ranges from several tens of μm to several hundreds of μm.

More specifically, the needle-shaped portion is required to penetrate the stratum corneum that is the outermost skin layer. The thickness of the stratum corneum is around 20 μm in average, although it depends on parts of a human body. Under the stratum corneum, there is an epiderm having a thickness ranging approximately 200 μm to 350 μm, and there is a dermis layer under the epiderm, where capillary vessels are reticulately spread. Therefore, a needle-shaped portion having a length of at least 20 μm or more is required to perforate the stratum corneum so that a liquid medicine is permeated. In the case where a needle-shaped body for blood sampling is manufactured, a needle-shaped body having a needle-shaped portion with a length of at least 350 μm or more is needed, considering the above-described structure of the skin.

As materials for the needle-shaped body, biocompatible resins including a medical silicone resin, maltose, polylactate, dextran, and the like are considered to be more suitable. If these materials are left in human body, the materials do not affect the human body. It should be noted that a technique of a needle-shaped body using a medical silicone resin or the like is known as disclosed in PTL 2, for example.

As a mechanism in which the needle-shaped body administers a medicine into a body, some mechanisms are proposed including a mechanism where a medicine is coated onto a needle and the needle is perforated into the skin, thereby administering the medicine, and a mechanism where a needle-shaped body having a hollow needle and a fine hole is used to administer a liquid medicine from a surface of the substrate to allow the liquid medicine to flow through the fine hole. It should be noted that these mechanisms are disclosed in PTL 3, for example.

As a forming process of a needle-shaped body, a method of manufacturing a needle-shaped body using a metal plate is known. The metal plate is expected to improve durability of the plate when the needle-shaped body is released from the plate. The forming process of a needle-shaped body using a metal plate is disclosed in PTL 4, for example.

However, when the needle-shaped body is formed using a metal plate, comparing with a forming process using a resin plate, forming properties of a needle-shaped portion and a releasing properties of a needle-shaped body may not have better performance, depending on materials applied to the needle-shaped body. Therefore, a resin plate may be unavoidably selected for forming the needle-shaped body, which however leads to a concern that the plate is broken when releasing the needle-shaped body because the resin plate has lower durability than the metal plate.

Effects of Present Embodiment (1) In contrast with a manufacturing method of a needle-shaped body according to a conventional technique having the above-described problems, the manufacturing method of the needle-shaped body 115 according to the present embodiment includes steps of: is provided with the needle-shaped portion 105 on the base portion 104, including a process for forming a needle-shaped body precursor 106 having a polygon at a portion contacting the base portion 104 of the needle-shaped portion 105; producing a needle-shaped body original plate 111 by forming the curved surface portion 110 at at least a part of apex portions of the polygon in the joint portion 107 which is a boundary portion between the base portion 104 and the needle-shaped portion 105 of the needle-shaped precursor 106; producing the resin plate 113 provided with the concave pattern 113a corresponding to the curved surface portion 110 and the needle-shaped portion 105 of the needle-shaped body original plate 111; and producing the needle-shaped body 115 provided with the needle-shaped portion 205 and the curved surface portion 210 obtained by transferring shapes of the needle-shaped portion 105 and the curved surface portion 110 by transfer-molding using the resin plate 113.

According to this configuration, since the concave pattern 113a has a concave portion corresponding to the curved surface portion 110, the resin plate 113 can be prevented from being distorted in the vicinity of the apex portion of the polygon included in the needle-shaped portion 115, when the transfer-molded needle-shaped body 115 is released. Therefore, according to the manufacturing method of the needle-shaped body 115 of the present embodiment, durability of the resin plate 113 can be enhanced and frequency of replacing the resin plate 113 can be reduced compared with a manufacturing method of a needle-shaped body according to a conventional technique. Hence, the productivity of the needle-shaped body 115 can be improved.

(2) The curved surface portion 110 may be formed by dropping the curved surface-forming material 109.

According to this configuration, since the curved surface portion 110 is formed by dropping the curved surface-forming material 109, the curved surface portion 110 can be readily and reliably formed at a desired portion.

(3) The cross-sectional shape of the curved surface portion 110 taken along a thickness direction of the base portion 104 may be a convex shape.

According to this configuration, since the cross-sectional shape of the curved surface portion 110 has a convex shape, the resin plate 113 can be prevented from being distorted in the vicinity of the apex portion of the polygon included in the needle-shaped portion 115, when the transfer-molded needle-shaped body 115 is released.

(4) The needle-shaped body 115 may be formed using a biocompatible material.

According to this configuration, if the needle-shaped portion 205 included in the needle-shaped body 115 is broken when perforating the skin, and remains in the body, there is no harm.

(5) The needle-shaped body 115 according to the present embodiment is provided with the base portion 204, the needle-shaped portion 205 formed on the base portion 204, and the curved surface portion 210 formed at at least a part of the joint portion 207 which is a boundary portion between the base portion 204 and the needle-shaped portion 205, wherein a portion contacting the base portion 204 of the needle-shaped portion 205 is a polygon, and the curved surface portion 210 is formed on the apex portion of the polygon of the joint portion 207.

According to this configuration, the needle-shaped body 115 is provided with the curved surface portion 210 which reinforces the needle-shaped portion 205 and the base portion 204 when the needle-shaped body 115 punctures the skin. Thus, the needle-shaped portion 205 is unlikely to be broken.

(6) The cross-sectional shape of the curved surface portion 210 taken along a thickness direction of the base portion 204 may be a convex shape.

According to this configuration, the needle-shaped portion 205 is more unlikely to be broken when the needle-shaped body 115 punctures the skin.

(7) The curved surface portion 210 having a convex shape may be selectively formed on an apex portion of the polygon of the junction portion 207.

According to this configuration, since the size of the curved surface portion 210 can be controlled, depth of puncture into the skin can be controlled.

In a manufacturing method of the above-mentioned needle-shaped body, for example, a transfer-molded needle-shaped body is released from a resin plate to produce a needle-shaped body.

However, the above-described conventional manufacturing method has problems, e.g., durability of the plate is low when the needle-shaped body is released from the resin plate, and productivity of the needle-shaped body is low as well.

An aspect of the present invention can provide a manufacturing method of a needle-shaped body and a needle-shaped body, capable of improving durability of a resin plate when a needle-shaped body is released therefrom in a forming process of the needle-shaped body using the resin plate, and improving the productivity.

To solve the above-described problems, a manufacturing method of a needle-shaped body according to an aspect of the present invention is characterized in that the method includes: a process of forming a needle-shaped body precursor provided with a base portion and a needle-shaped portion on the base portion, a portion of the needle-shaped portion contacting the base portion being formed into a polygon; a process of producing a needle-shaped body original plate by forming a curved surface portion at at least a part of apex portions of the polygon in a junction portion, the junction portion being a boundary portion between the base portion and the needle-shaped portion in the needle-shaped body precursor; a process of producing a resin plate by a transfer molding using the needle-shaped body original plate, the resin plate being provided with a concave pattern corresponding to the needle-shaped portion and the curved surface portion in the needle-shaped body original plate; and a process of producing a needle-shaped body by a transfer molding using the resin plate, the needle-shaped body being provided with a transfer needle-shaped portion and a transferred curved surface portion, where shapes of the needle-shaped portion and the curved surface portion are transferred thereto.

According to the above-described aspect of the invention, in a manufacturing method of a needle-shaped body using a resin plate, and a needle-shaped body, durability of the resin plate when the needle-shaped body is released therefrom can be improved and productivity of the needle-shaped body can be improved.

The manufacturing method of the needle-shaped body according to an aspect of the present invention is applicable not only to medical area but also to various areas which require fine needle-shaped bodies. For example, the manufacturing method according to an aspect of the present invention is useful for producing fine needle-shaped bodies used in MEMS devices, optical devices, drug development, cosmetics, beauty applications or the like.

REFERENCE SIGNS LIST

101, 103: silicon substrate
102: ground groove
104, 204: base portion
104*a*: upper surface
105, 205: needle-shaped portion
106: needle-shaped body precursor
107, 207: junction portion
108: dispenser
109: curved surface-forming material
110, 210: curved surface portion
111: needle-shaped body original plate
112: resin plate material
113: resin plate
113*a*: concave pattern
115: needle-shaped body Obviously, numerous modifications and variations of the present invention are possible in light of the above teachings. It is therefore to be understood that within the scope of the appended claims, the invention may be practiced otherwise than as specifically described herein.

What is claimed is:

1. A method of manufacturing a needle-shaped body, comprising:
    forming a needle-shaped body precursor such that the needle-shaped body precursor has a base portion and a needle-shaped portion having a form of a polygon and formed on the base portion, and that the needle-shaped portion has a plurality of joint portions which directly contacts the base portion;
    producing a needle-shaped body original plate by forming a plurality of curved surface portions in a plurality of apex portions of the polygon at a boundary between the base portion and the needle-shaped portion in the needle-shaped body precursor;
    producing a resin plate by transfer molding with the needle-shaped body original plate such that the resin plate has a concave pattern corresponding to the needle-shaped portion and the curved surface portions in the needle-shaped body original plate; and producing a needle-shaped body by transfer molding with the resin plate such that the needle-shaped body has a transferred needle-shaped portion having a shape of the needle-shaped portion transferred and a plurality of transferred curved surface portions having a shape of the curved surface portions transferred.

2. The method of claim 1, wherein the plurality of curved surface portions is formed by dropping a curved surface-forming material.

3. The method of claim 2, wherein the plurality of curved surface portions is formed such that a cross-sectional shape of each of the curved surface portions taken along a thickness direction of the base portion is a convex shape.

4. The method of claim 2, wherein the producing of the needle-shaped body comprises producing the needle-shaped body comprising a biocompatible material.

5. The method of claim 1, wherein the plurality of curved surface portions is formed such that a cross-sectional shape of each of the curved surface portions taken along a thickness direction of the base portion is a convex shape.

6. The method of claim 5, wherein the producing of the needle-shaped body comprises producing the needle-shaped body comprising a biocompatible material.

7. The method of claim 1, wherein the producing of the needle-shaped body comprises producing the needle-shaped body comprising a biocompatible material.

8. A needle-shaped body, comprising:
a base portion;
a needle-shaped portion formed on the base portion and having a form of polygon;
a plurality of curved surface portions formed at a boundary between the base portion and the needle-shaped portion,
wherein the needle-shaped portion has a plurality of joint portions which directly contacts the base portion such that the plurality of curved surface portions is formed in a plurality of apex portions of the polygon at the boundary between the base portion and the needle-shaped portion and that each of the joint portions is formed between the curved surface portions.

9. The needle-shaped body of claim 8, wherein a cross-sectional shape of each of the curved surface portions taken along a thickness direction of the base portion is a convex shape.

10. The needle-shaped body of claim 9, wherein the plurality of curved surface portions is selectively formed in the plurality of apex portions of the polygon.

11. The needle-shaped body of claim 9, wherein the needle-shaped portion has a height $L1$ of from 50 μm to 2000 μm where the height $L$ is from a surface of the base portion to an apex portion of the needle-shaped portion, and the needle-shaped portion has a height $L2$ of from $L1 \times 0.05$ to $L1 \times 0.5$ where the height $L2$ is from the surface of the base portion to a highest portion of each of the curved surface portions.

12. The needle-shaped body of claim 9, wherein the plurality of curved surface portions is formed in the plurality of apex portions of the polygon at the boundary between the base portion and the needle-shaped portion, respectively.

13. The needle-shaped body of claim 9, wherein the plurality of curved surface portions includes at least one curved surface portions formed across adjacent apex portions of the plurality of apex portions of the polygon at the boundary between the base portion and the needle-shaped portion, respectively.

14. The needle-shaped body of claim 8, wherein a cross-sectional shape of each of the curved surface portions taken along a thickness direction of the base portion is a concave shape.

15. The needle-shaped body of claim 14, wherein the plurality of curved surface portions is selectively formed in the plurality of apex portions of the polygon.

16. The needle-shaped body of claim 14, wherein the needle-shaped portion has a height $L1$ of from 50 μm to 2000 μm where the height $L$ is from a surface of the base portion to an apex portion of the needle-shaped portion, and the needle-shaped portion has a height $L2$ of from $L1 \times 0.05$ to $L1 \times 0.5$ where the height $L2$ is from the surface of the base portion to a highest portion of each of the curved surface portions.

17. The needle-shaped body of claim 8, wherein the plurality of curved surface portions is selectively formed in the plurality of apex portions of the polygon.

18. The needle-shaped body of claim 8, wherein the needle-shaped portion has a height $L1$ of from 50 μm to 2000 μm where the height $L$ is from a surface of the base portion to an apex portion of the needle-shaped portion, and the needle-shaped portion has a height $L2$ of from $L1 \times 0.05$ to $L1 \times 0.5$ where the height $L2$ is from the surface of the base portion to a highest portion of each of the curved surface portions.

19. The needle-shaped body of claim 8, wherein the plurality of curved surface portions is formed in the plurality of apex portions of the polygon at the boundary between the base portion and the needle-shaped portion, respectively.

20. The needle-shaped body of claim 8, wherein the plurality of curved surface portions includes at least one curved surface portions formed across adjacent apex portions of the plurality of apex portions of the polygon at the boundary between the base portion and the needle-shaped portion, respectively.

* * * * *